（12） United States Patent
Cummings

(10) Patent No.: US 9,683,978 B2
(45) Date of Patent: Jun. 20, 2017

(54) SYSTEMS AND METHODS FOR DETECTING WATER/PRODUCT INTERFACES DURING FOOD PROCESSING

(71) Applicant: Nestec S.A., Vevey (CH)

(72) Inventor: Daniel Louis Cummings, Fremont, MI (US)

(73) Assignee: Nestec S.A., Vevey (CH)

( * ) Notice: Subject to any disclaimer, the term of this patent is extended or adjusted under 35 U.S.C. 154(b) by 131 days.

(21) Appl. No.: 14/272,673

(22) Filed: May 8, 2014

(65) Prior Publication Data

US 2014/0356493 A1 Dec. 4, 2014

Related U.S. Application Data

(60) Provisional application No. 61/829,406, filed on May 31, 2013, provisional application No. 61/899,053, filed on Nov. 1, 2013.

(51) Int. Cl.
*A23L 3/00* (2006.01)
*G01N 33/02* (2006.01)
(Continued)

(52) U.S. Cl.
CPC .............. *G01N 33/02* (2013.01); *A23L 3/001* (2013.01); *A23L 3/003* (2013.01); *B65B 25/001* (2013.01);
(Continued)

(58) Field of Classification Search
CPC ...... G01N 33/02; G01N 15/06; G01N 29/036; G01N 29/02; G01N 2015/0065; G01N 2015/0687; G01N 2291/2636; G01N 2291/02809; G01N 2291/017; G01N 15/02; G01N 2291/022; G01F 1/663;
(Continued)

(56) References Cited

U.S. PATENT DOCUMENTS 3,040,562 A * 6/1962 Fitzgerald .............. G01N 29/02
367/114
3,891,779 A * 6/1975 Robinson .................. A23L 3/02
422/28
(Continued)

FOREIGN PATENT DOCUMENTS

WO 0206816 A1 1/2002

OTHER PUBLICATIONS

International Search Report and Written Opinion from corresponding PCT patent application No. PCT/IB2014/061307 dated Sep. 9, 2014.

*Primary Examiner* — Drew Becker
(74) *Attorney, Agent, or Firm* — Gary M. Lobel, Esq.

(57) ABSTRACT

The present disclosure provides systems and methods for manufacturing food products. In a general embodiment, systems for manufacturing a food product include at least one heat exchanger, at least one food product tank, at least one conduit downstream of the food product tank for flow of the food product, and a flow detection device coupled to an exterior of the conduit. The flow detection device includes a processor and a computer readable medium storing instructions which, when executed, cause the processor to perform a spread spectrum analysis of the flow of the food product through the conduit. Methods for manufacturing food products are also provided.

15 Claims, 1 Drawing Sheet

(51) Int. Cl.
  *G01F 1/66*     (2006.01)
  *G01N 29/02*    (2006.01)
  *B65B 25/00*    (2006.01)
  *B65B 55/02*    (2006.01)
  *G01N 29/036*   (2006.01)
  *G01N 15/06*    (2006.01)
  *A23L 23/00*    (2016.01)
  *G01N 15/02*    (2006.01)
  *G01N 15/00*    (2006.01)

(52) U.S. Cl.
  CPC ............ B65B 55/025 (2013.01); G01F 1/663 (2013.01); G01N 15/06 (2013.01); G01N 29/02 (2013.01); G01N 29/036 (2013.01); *A23L 23/00* (2016.08); *G01N 15/02* (2013.01); *G01N 2015/0065* (2013.01); *G01N 2015/0687* (2013.01); *G01N 2291/017* (2013.01); *G01N 2291/022* (2013.01); *G01N 2291/02809* (2013.01); *G01N 2291/2636* (2013.01)

(58) Field of Classification Search
  CPC .......... A23L 3/001; A23L 3/003; A23L 23/00; B65B 25/001; B65B 55/025
  USPC ............. 426/238, 231, 399; 73/61.71–61.75, 73/64.53, 570–672
  See application file for complete search history.

(56) References Cited

U.S. PATENT DOCUMENTS

| | | | |
|---|---|---|---|
| 5,473,934 A * | 12/1995 | Cobb | G01N 29/024 73/597 |
| 6,136,362 A * | 10/2000 | Ashton | A23C 7/02 134/169 R |
| 6,323,033 B1 * | 11/2001 | van den Berg | A01J 7/022 134/18 |
| 6,481,268 B1 * | 11/2002 | Povey | G01N 15/02 702/190 |
| 6,874,356 B2 * | 4/2005 | Kornfeldt | C12M 29/18 73/32 A |
| 7,368,139 B1 * | 5/2008 | Bronnert | A23L 3/225 137/15.05 |
| 8,652,552 B2 * | 2/2014 | Argudayev | G01N 29/024 426/231 |
| 2002/0005071 A1 * | 1/2002 | Song | G01S 15/8954 73/606 |
| 2003/0051535 A1 * | 3/2003 | Coupland | G01N 29/022 73/64.53 |
| 2004/0006409 A1 * | 1/2004 | Liljenberg | G01N 29/032 700/266 |
| 2005/0215902 A1 | 9/2005 | Greenwood | |
| 2006/0178581 A1 * | 8/2006 | Africk | G01N 15/02 600/440 |
| 2006/0196529 A1 * | 9/2006 | Kenowski | B08B 9/0325 134/56 R |
| 2007/0119239 A1 * | 5/2007 | Priev | G01N 15/06 73/61.75 |
| 2009/0272190 A1 * | 11/2009 | Hofmann | G01N 29/032 73/599 |
| 2009/0324790 A1 * | 12/2009 | Hilgren | A22B 7/008 426/335 |
| 2011/0083494 A1 * | 4/2011 | Van Halsema | A01J 5/0137 73/64.53 |
| 2011/0197920 A1 * | 8/2011 | Kenowski | B08B 9/027 134/10 |
| 2012/0276266 A1 | 11/2012 | Tacke | |
| 2014/0087035 A1 * | 3/2014 | Cummings | A23L 3/02 426/232 |
| 2014/0238116 A1 * | 8/2014 | Kwan | G01F 1/667 73/61.79 |
| 2014/0348998 A1 * | 11/2014 | Hoffmann | A23C 3/02 426/491 |

* cited by examiner

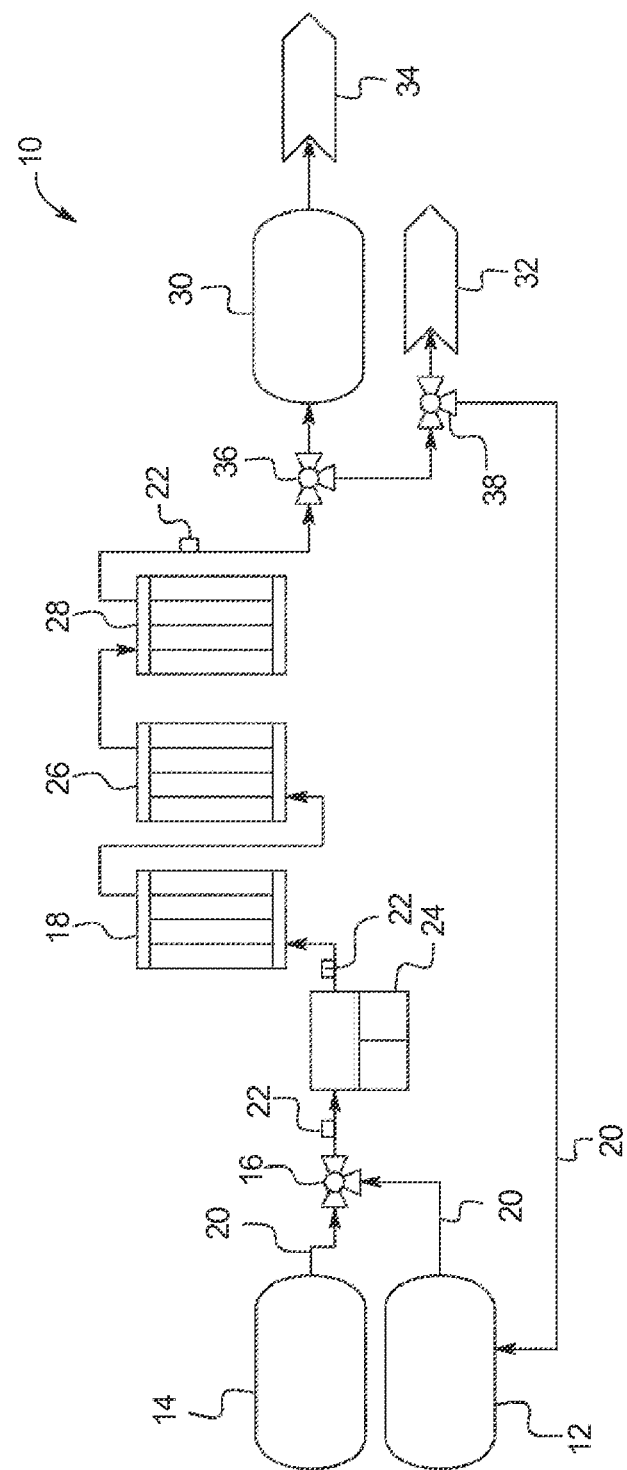

SYSTEMS AND METHODS FOR DETECTING WATER/PRODUCT INTERFACES DURING FOOD PROCESSING

BACKGROUND

The present disclosure relates generally to food technology. More specifically, the present disclosure relates to systems and methods for detecting the water to product interface that occurs during a transition from recirculating water to a food product during aseptic processing of the food product.

Methods of aseptically processing food products are well known. These methods, however, may not always provide optimal results for manufacturing efficiency and/or resulting product quality. For example, during aseptic processing, a food product is typically heated by water, which is heated by steam. Prior to processing of the food product, however, the system is chemically cleaned and rinsed with water. Water is then recirculated through the system to maintain sterility of the system. When the timing is appropriate to introduce the food product into the system, a product tank valve is opened and the initial water/food product interface begins to travel through the system. Alternatively, when timing is appropriate to cease flow of the food product in the system, a product tank valve is closed and water begins recirculating through the system again. In either instance, it is important to detect the location of the water/product or product/water interface to avoid process inefficiencies such as, for example, the unnecessary loss of product that occurs when a conservative approach to food product packaging is taken. In this regard, factories may take a conservative approach to evaluating the timing of the water/product interface to ensure that no diluted product is packaged for sale to consumers.

Therefore, there exists a need for a manufacturing process that is able to accurately detect the water/food product interface that occurs during aseptic processing of a food product.

SUMMARY

In the present disclosure, systems and methods for manufacturing aseptic food products are provided. In an embodiment, systems for manufacturing a food product are provided and include at least one heat exchanger, at least one food product tank, at least one conduit downstream of the food product tank for flow of the food product, and a flow detection device coupled to an exterior of the conduit. The flow detection device includes a processor and a computer readable medium storing instructions which, when executed, cause the processor to perform a spread spectrum analysis of the flow of the food product through the conduit.

In an embodiment, the system is an aseptic manufacturing system.

In an embodiment, the flow detection device is an ultrasonic flow detection device.

In an embodiment, the conduit is tubing. The conduit may be made of a material selected from the group consisting of cast iron, mild steel, rigid plastic, stainless steel, or combinations thereof. In an embodiment, the conduit is made of stainless steel. The conduit can connect the food product tank to the heat exchanger.

In an embodiment, the system includes at least one additional conduit for flow of the food product. At least one of the additional conduits may have a flow detection device. Alternatively, each of the additional conduits may have a flow detection device.

In an embodiment, the instructions are programmed to cause the computer processor to transmit an ultrasounic beam from the flow detection device and through the conduit, wherein the beam is (i) refracted by a wall of the conduit and/or (ii) reflected by particles in the food product and received by the flow detection device.

In an embodiment, the instructions are programmed to cause the computer processor to analyze the refracted and/or reflected beams to determine a concentration of the food product.

In an embodiment, the instructions are programmed to cause the computer processor to detect a change from a low particle concentration of the food product to a high particle concentration of the food product.

In another embodiment, systems for manufacturing a food product are provided and include at least one heat exchanger, at least one food product tank, tubing connecting at least the food product tank to the heat exchanger, a computer having a computer processor, and a computer-readable medium accessible to the computer and containing a software program therein that is programmed to cause the computer processor to detect a change from a low particle concentration of the food product to a high particle concentration of the food product when the food product flows through the tubing.

In an embodiment, the computer is a flow detection device.

In an embodiment, the system is an aseptic manufacturing system.

In an embodiment, the computer is an ultrasonic flow detection device.

In an embodiment, the computer is so constructed and arranged to perform a spread spectrum analysis.

In an embodiment, the tubing is made of a material selected from the group consisting of cast iron, mild steel, rigid plastic, stainless steel, or combinations thereof. In an embodiment, the tubing is made of stainless steel.

In an embodiment, the system includes additional tubing for flow of the food product. At least some of the additional tubing may have a flow detection device. Alternatively, all of the additional tubing may have a flow detection device.

In an embodiment, the instructions are programmed to cause the computer processor to transmit an ultrasounic beam from the flow detection device and through the tubing, wherein the beam is (i) refracted by a wall of the tubing and/or (ii) reflected by particles in the food product and received by the computer.

In an embodiment, the instructions are programmed to cause the computer processor to analyze the refracted and/or reflected beams to determine a concentration of the food product.

In yet another embodiment, methods for manufacturing a food product are provided and include providing a food processing system having at least one heat exchanger, at least one food product tank, at least one conduit downstream of the food product tank for flow of the food product, and a flow detection device coupled to an exterior of the conduit. The flow detection device has a processor and a computer readable medium storing instructions which, when executed, cause the processor to perform a spread spectrum analysis of the flow of the food product through the conduit. The methods further include initiating flow of the food product through the conduit.

In an embodiment, the system is an aseptic manufacturing system.

In an embodiment, the flow detection device is an ultrasonic flow detection device.

In an embodiment, the conduit is tubing. The conduit may be made of a material selected from the group consisting of cast iron, mild steel, rigid plastic, stainless steel, or combinations thereof. In an embodiment, the conduit is made of stainless steel.

In an embodiment, the conduit connects the food product tank to the heat exchanger.

In an embodiment, the system includes at least one additional conduit for flow of the food product. At least one of the additional conduits may have a flow detection device. Alternatively, each of the additional conduits may have a flow detection device.

In an embodiment, the instructions are programmed to cause the computer processor to transmit an ultrasounic beam from the flow detection device and through the conduit, wherein the beam is (i) refracted by a wall of the conduit and/or (ii) reflected by particles in the food product and received by the flow detection device.

In an embodiment, the instructions are programmed to cause the computer processor to analyze the refracted and/or reflected beams to determine a concentration of the food product.

In an embodiment, the instructions are programmed to cause the computer processor to detect a change from a low particle concentration of the food product to a high particle concentration of the food product.

In still yet another embodiment, methods for manufacturing a food product are provided and include providing a food processing system having at least one heat exchanger, at least one food product tank, tubing connecting at least the food product tank to the heat exchanger, a computer having a computer processor, and a computer-readable medium accessible to the computer and containing a software program therein that is programmed to cause the computer processor to detect a change from a low particle concentration of the food product to a high particle concentration of the food product when the food product flows through the tubing. The methods further include initiating flow of the food product through the tubing.

In an embodiment, the computer is a flow detection device.

In an embodiment, the system is an aseptic manufacturing system.

In an embodiment, the computer is an ultrasonic flow detection device. The ultrasonic flow detection device may be so constructed and arranged to perform a spread spectrum analysis.

In an embodiment, the tubing is made of a material selected from the group consisting of cast iron, mild steel, rigid plastic, stainless steel, or combinations thereof. In an embodiment, the tubing is made of stainless steel.

In an embodiment, they system further includes additional tubing connecting the heat exchanger to other devices in the aseptic manufacturing system. The other devices are selected from the group consisting of tanks, valves, exchangers, or combinations thereof. The additional tubing may have at least one computer.

In an embodiment, the instructions are programmed to cause the computer processor to transmit an ultrasounic beam from the computer and through the tubing, wherein the beam is (i) refracted by a wall of the tubing and/or (ii) reflected by particles in the food product and received by the computer.

In an embodiment, the instructions are programmed to cause the computer processor to analyze the refracted and/or reflected beams to determine a concentration of the food product.

In another embodiment, methods for detecting a water/food product interface are provided. The methods include providing a food processing system having at least one heat exchanger, at least one food product tank, tubing connecting at least the food product tank to the heat exchanger, a computer having a computer processor, and a computer-readable medium accessible to the computer and containing a software program therein that is programmed to cause the computer processor to detect a change from a low particle concentration of the food product to a high particle concentration of the food product when the food product flows through the tubing. The methods further include initiating flow of the food product through the tubing and executing the software program.

In an embodiment, the computer is a flow detection device.

In an embodiment, the system is an aseptic manufacturing system.

In an embodiment, the computer is an ultrasonic flow detection device. The computer may be so constructed and arranged to perform a spread spectrum analysis.

In an embodiment, the tubing is made of a material selected from the group consisting of cast iron, mild steel, rigid plastic, stainless steel, or combinations thereof. In an embodiment, the tubing is made of stainless steel.

In an embodiment, the system includes additional tubing connecting the heat exchanger to other devices in the aseptic manufacturing system. The other devices are selected from the group consisting of tanks, valves, exchangers, or combinations thereof. The additional tubing may have at least one flow detection device.

In an embodiment, the instructions are programmed to cause the computer processor to transmit an ultrasounic beam from the computer and through the tubing, wherein the beam is (i) refracted by a wall of the tubing and/or (ii) reflected by particles in the food product and received by the computer.

In an embodiment, the instructions are programmed to cause the computer processor to analyze the refracted and/or reflected beams to determine a concentration of the food product.

An advantage of the present disclosure is to provide improved food manufacturing processes.

Another advantage of the present disclosure is to provide improved aseptic food processing procedures.

Yet another advantage of the present disclosure is to provide methods for manufacturing a food product that detect the location of a water/food product interface.

Still yet another advantage of the present disclosure is to provide methods for manufacturing a food product that reduce the risk of packaging a diluted food product.

Yet another advantage of the present disclosure is to provide methods for controlling an aseptic food product manufacturing line.

Additional features and advantages are described herein, and will be apparent from the following Detailed Description and the FIGURES.

BRIEF DESCRIPTION OF THE FIGURES

FIG. 1 shows a schematic representation of a food manufacturing process in accordance with an embodiment of the present disclosure.

DETAILED DESCRIPTION

As used in this disclosure and the appended claims, the singular forms "a," "an" and "the" include plural referents unless the context clearly dictates otherwise.

As used herein, "about" is understood to refer to numbers in a range of numerals. Moreover, all numerical ranges herein should be understood to include all integer, whole or fractions, within the range.

As used herein, "recirculating water" is understood to mean water that is recirculating in the portion of a heat exchanger that will contain a food product during processing of the food product. The skilled artisan will appreciate that prior to processing of a food product the system is chemically cleaned and rinsed with water and water is then recirculated through the system to keep the system sterile. When the timing is appropriate to introduce the food product into the system, a product tank valve is opened and the initial recirculating water/food product interface begins to travel through the system, thereby displacing the recirculating water.

As used herein, "spread spectrum analysis" is a technique that may be used in flow monitoring and includes the use of a wide ultrasonic beam that is refracted by a conduit wall and is also reflected by particles suspended in the flowing media (e.g., a food product). More specifically, the wide ultrasonic beam is transmitted from a tangentially mounted output ceramic of a flow meter and through the conduit wall at an angle of about 90° to the flow through the conduit. The beam is then refracted at angles across the axis of the flow and subsequently reflected from any particles, bubbles, etc. in the flowing media in all directions and at a wide range of frequencies. The multiple reflections are received by a second receiver ceramic present in the flow meter. The returned signals may be analyzed using a specific digital signal processing platform (e.g., software) to derive the desired flow information.

Methods of aseptically processing food products are well known. These methods, however, may not always provide optimal results for manufacturing efficiency and/or resulting product quality. For example, during aseptic processing, a food product is typically heated by water, which is heated by steam. Prior to processing of the food product, however, the system is chemically cleaned and rinsed with water. Water is then recirculated through the system to keep the system sterile. When the timing is appropriate to introduce the food product into the system, a product tank valve is opened and the initial water/food product interface begins to travel through the system. Alternatively, when timing is appropriate to cease flow of the food product in the system, a product tank valve is closed and water begins recirculating through the system again. In either instance, it is important to detect the location of the water/product or product/water interface to avoid process inefficiencies such as, for example, the unnecessary loss of product and/or energy that occurs when a conservative approach to food product packaging is taken. In this regard, factories may take a conservative approach to evaluating the timing of the water/product interface to ensure that no diluted product is packaged for sale to consumers.

Current methods for detecting the water/product interface use known instruments such as optical, density, or viscosity measurement, which require the detectors to be in direct contact with the product. This presents issues not only for the construction of the system, but also for the sterility of the aseptic processing system.

Another option for detecting the water/product interface includes ultrasonic detectors such as ultrasonic flow meters. Conventional ultrasonics, however, do not work reliably with the sanitary stainless steel tubing that is typically used in aseptic processing. In this regard, the stainless steel tubing can vibrate during use, which causes significant interference with the signals of a conventional ultrasonic flow meter/detector.

Accordingly, the systems and methods of the present disclosure utilize flow detection devices that are specifically configured to operate in an aseptic manufacturing environment. More specifically, the flow detection devices of the present disclosure utilize a new signal processing algorithm that is able to overcome the previously mentioned installation issues. The processing algorithm is a spread spectrum analysis that works by detecting a size and concentration of solid particles in a liquid. Accordingly, a flow detection device programmed with instructions for executing the spread spectrum analysis is able to exploit the change in signal quality from water (with an extremely low particle concentration) to product (with a relative high particle concentration) to detect the passage of the water/product interface.

As shown in FIG. 1, a schematic representation of an aseptic food manufacturing process 10 is illustrated, which includes, but is not limited to, a water tank 12, a food product tank 14, a valve 16, a heat exchanger 18, and conduits 20 connecting the elements of the process. Conduits 20 may be stainless steel conduits. However, the skilled artisan will appreciate that the conduits may also be made of a material such as, for example, cast iron, mild steel, rigid plastic, etc. The skilled artisan will also appreciate that the manufacturing line need not be limited to the illustrated devices and may include, for example, other tanks, valves, conduits, heat exchangers, pumps, holding tanks, coolers, surge tanks, drains, packaging equipment, etc. For example, and as shown in FIG. 1, process 10 may also include pump 24, hold tank 26, cooler 28, aseptic surge tank 30, drain 32, packaging equipment 34 and additional valves 36, 38.

As is also shown in FIG. 1, flow detection devices 22 may be located on an external portion of any tubing 20 present in the manufacturing line. In this regard, a single manufacturing line may have one flow detection device or a plurality of flow detection devices located along any portion of conduit in the process. Providing a plurality of detection devices allows a manufacturing operator to detect the location of a water/product or product/water interface at any location along the manufacturing line. This increased detection ability would greatly reduce the amount of wasted energy or product that is currently seen in aseptic process manufacturing lines. The skilled artisan will appreciate that flow detection devices 22 need not be located at the illustrated places in the process and may be located along any portion of conduit 20 in the process.

Accordingly, the processes and methods of the present disclosure advantageously reduce the amount of wasted food and/or energy that is seen in known aseptic manufacturing processes. Additionally, the systems and methods of the present disclosure provide the advantages of decreased risk of contamination by using an externally mounted flow detection device, and ease of construction of the manufacturing line.

Although the present disclosure is discussed as being utilized in the manufacture of, for example, an aseptic food product through a heat exchanger that is heated by a heating medium, the skilled artisan will appreciate that the presently disclosed methods and processes are not limited to the manufacture of an aseptic food product. Further, although the present disclosure contains discussions of the processing of food products, the skilled artisan will appreciate that any products that have a particle concentration that is greater than water may be processed according to the systems and methods disclosed herein.

Further, although the phrases "flow meter" and "flow detection device" are used at various places in the present disclosure, the skilled artisan will appreciate that the devices can also be referred to as computers that are specifically programmed to detect flow rates. Accordingly, the phrases "flow meter," "flow detection device," and "computer" may be used interchangeably in the present specification.

In an embodiment of the present disclosure, methods for manufacturing a food product are provided and include providing a food processing system having at least one heat exchanger, at least one food product tank, at least one conduit downstream of the food product tank for flow of the food product, and a flow detection device coupled to an exterior of the conduit. The flow detection device has a processor and a computer readable medium storing instructions which, when executed, cause the processor to perform a spread spectrum analysis of the flow of the food product through the conduit. The methods further include initiating flow of the food product through the conduit.

In yet another embodiment, methods for manufacturing a food product are provided and include providing a food processing system having at least one heat exchanger, at least one food product tank, tubing connecting at least the food product tank to the heat exchanger, a computer having a computer processor, and a computer-readable medium accessible to the computer and containing a software program therein that is programmed to cause the computer processor to detect a change from a low particle concentration of the food product to a high particle concentration of the food product when the food product flows through the tubing. The methods further include initiating flow of the food product through the tubing.

In another embodiment, methods for detecting a water/food product interface are provided. The methods include providing a food processing system having at least one heat exchanger, at least one food product tank, tubing connecting at least the food product tank to the heat exchanger, a computer having a computer processor, and a computer-readable medium accessible to the computer and containing a software program therein that is programmed to cause the computer processor to detect a change from a low particle concentration of the food product to a high particle concentration of the food product when the food product flows through the tubing. The methods further include initiating flow of the food product through the tubing and executing the software program.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method for detecting a water/food product interface in an aseptic manufacturing system, the method comprising:
   initiating flow in a conduit in an aseptic food manufacturing system;
   operating an ultrasonic flow detection device transmitting an ultrasonic beam through a wall of the conduit, wherein the ultrasonic beam is refracted at angles from the wall of the conduit and reflected from particles present in the conduit at a range of angles and frequencies, and measuring returned reflected signals; and
   analyzing the measured returned reflected signals to determine a change in particle concentration indicating a water/food product interface.

2. The method according to claim 1, wherein the step of analyzing the measured returned signals includes executing software program instructions which, when executed, cause a computer processor to analyze the measured returned signals to determine a change in particle concentration indicating the water/food product interface.

3. The method according to claim 1, further comprising executing software program instructions which, when executed, cause a computer processor to initiate transmission of an ultrasonic beam from the flow detection device and through the conduit, wherein the beam is (i) refracted by a wall of the conduit and/or (ii) reflected by particles in the conduit and received by the ultrasonic flow detection device.

4. The method according to claim 3, further comprising executing software program instructions which, when executed, cause the computer processor to analyze the refracted and/or reflected beams to determine a food product concentration in the conduit.

5. The method according to claim 3, wherein the ultrasonic flow detection device is so constructed and arranged to perform a spread spectrum analysis.

6. The method according to claim 1, wherein the aseptic food manufacturing system comprises additional conduit connecting a heat exchanger to other devices in the aseptic food manufacturing system, wherein the other devices are selected from the group consisting of tanks, valves, heat exchangers, and combinations thereof, and, wherein the software program includes instructions which, when executed, cause the computer processor to initiate transmission of an ultrasonic beam from the flow detection device and through at least one of the additional conduit, wherein the beam is (i) refracted by a wall of the conduit and/or (ii) reflected by particles in the conduit and received by the flow detection device.

7. The method according to claim 6, further comprising executing software program instructions which, when executed, cause the computer processor to analyze the refracted and/or reflected beams to determine a food product concentration in the conduit.

8. The method according to claim 6, wherein the ultrasonic flow detection device is so constructed and arranged to perform a spread spectrum analysis.

9. The method according to claim 1, wherein the aseptic food manufacturing system comprises:
   at least one heat exchanger;
   at least one food product tank;
   at least one conduit downstream of the food product tank for flow of a food product, wherein the conduit connects the food product tank to the heat exchanger; and
   wherein the ultrasonic flow detection device is coupled to an exterior of the conduit, the ultrasonic flow detection device comprising a processor and a computer readable medium storing instructions which, when executed, cause the processor to perform a spread spectrum analysis of the flow of the food product through the conduit.

10. The method according to claim 9, further comprising at least one additional conduit for flow of the food product, wherein at least one of the additional conduits comprises a flow detection device.

11. The method according to claim 9, wherein the instructions are programmed to cause the processor to initiate transmission of an ultrasonic beam from the flow detection device and through the conduit, wherein the beam is (i) refracted by a wall of the conduit and/or (ii) reflected by particles in the conduit and received by the flow detection device.

12. The method according to claim 11, wherein the instructions are programmed to cause the processor to analyze the refracted and/or reflected beams to determine a food product concentration in the conduit.

13. The method according to claim 9, wherein the instructions are programmed to cause the processor to detect a change from a low particle concentration to a high particle concentration in the conduit.

14. The method according to claim 9, further comprising additional flow paths connecting other devices in the aseptic food manufacturing system, wherein the other devices are selected from the group consisting of tanks, valves, exchangers, and combinations thereof.

15. The method according to claim 9, wherein the instructions are programmed to cause initiating flow of the food product through the conduit.

\* \* \* \* \*